United States Patent [19]
Gustafson et al.

[11] Patent Number: 5,478,527
[45] Date of Patent: Dec. 26, 1995

[54] HIGHLY REFLECTIVE BIOGRATINGS

[75] Inventors: Eric K. Gustafson, Palo Alto; John Lee, Cupertino; Yuh-Geng Tsay, Los Altos Hills, all of Calif.

[73] Assignee: Adeza Biomedical Corporation, Sunnyvale, Calif.

[21] Appl. No.: 342,486

[22] Filed: Nov. 21, 1994

Related U.S. Application Data

[63] Continuation of Ser. No. 963,249, Oct. 19, 1992, abandoned, which is a continuation of Ser. No. 525,828, May 17, 1990, abandoned.

[51] Int. Cl.$^6$ .................................................. G01N 33/545
[52] U.S. Cl. .................. 422/82.11; 422/58; 436/164; 436/805; 436/531
[58] Field of Search .................................. 428/433, 434; 435/7; 436/527, 807, 519, 531, 164, 805; 422/58, 82.11

[56] References Cited

U.S. PATENT DOCUMENTS

| | | | |
|---|---|---|---|
| 4,521,522 | 6/1985 | Lundström et al. | 436/525 |
| 4,537,861 | 8/1985 | Elings et al. | 436/518 |
| 4,647,544 | 3/1987 | Nicoli et al. | 436/518 |
| 4,689,232 | 8/1987 | Moeschler | 424/195.1 |
| 4,756,834 | 7/1988 | Muller et al. | 210/635 |
| 4,876,208 | 10/1989 | Gustafson et al. | 436/531 |
| 4,886,761 | 12/1989 | Gustafson et al. | 436/518 |
| 5,089,387 | 2/1992 | Tsay et al. | 435/6 |

FOREIGN PATENT DOCUMENTS

| | | |
|---|---|---|
| 0100660 | 2/1984 | European Pat. Off. |
| 0112721 | 7/1984 | European Pat. Off. ............ 33/54 |
| 0178083 | 4/1986 | European Pat. Off. ............ 33/543 |
| 0266461 | 5/1988 | European Pat. Off. ...... G01N 33/543 |
| 86/01901 | 3/1986 | WIPO ................. G01N 33/543 |

OTHER PUBLICATIONS

Patent Abstracts Of Japan vol. 012, No. 307 (P–747) 22 Aug. 1988 & JP–A–63 078 051 (Teijin Ltd) 8 Apr. 1988 *abstract*.
Arwin et al, *Analytical Biochemistry*, 145:106–112 (1985).

*Primary Examiner*—Lyle A. Alexander
*Attorney, Agent, or Firm*—Skjerven, Morrill, MacPherson, Franklin & Friel; Laura Terlizzi

[57] ABSTRACT

A reflective biograting consists of an optically flat layer of a transparent composition such as silicon dioxide having a first and second surface, alternating zones of active and inactive binding reagent on the first surface, and a reflective metal layer having a thickness of at least above 1000 Å. The reflective metal layer can be supported on an optically flat surface of a wafer, and the reflective metal can be aluminum, silver, gold, chromium, nickel, titanium or platinum coating on a polished wafer. Preferably, the silicon dioxide layer is formed either by direct sputtering of silicon dioxide or by coating an alkali metal silicate solution on the surface of the reflective metal, optionally containing an aminoalkylsilane and a water-soluble hydroxylated polymer such as a dextran. Alternatively, the reflective support comprises one or more reflective layer units, each reflective layer unit comprising an optically flat layer of silicon, and preferably polysilicon, on a layer of silicon dioxide. Each layer of silicon has a thickness within the range of from 150 to 750 Å, from 850 to 1300 Å, or from 1700 to 2150 Å, and preferably within the range of from 200 to 600 Å. Each layer of silicon dioxide has a thickness within the range of from 800 to 1200 Å. The reflective support is supported on the substantially flat surface of an insoluble support.

9 Claims, 4 Drawing Sheets

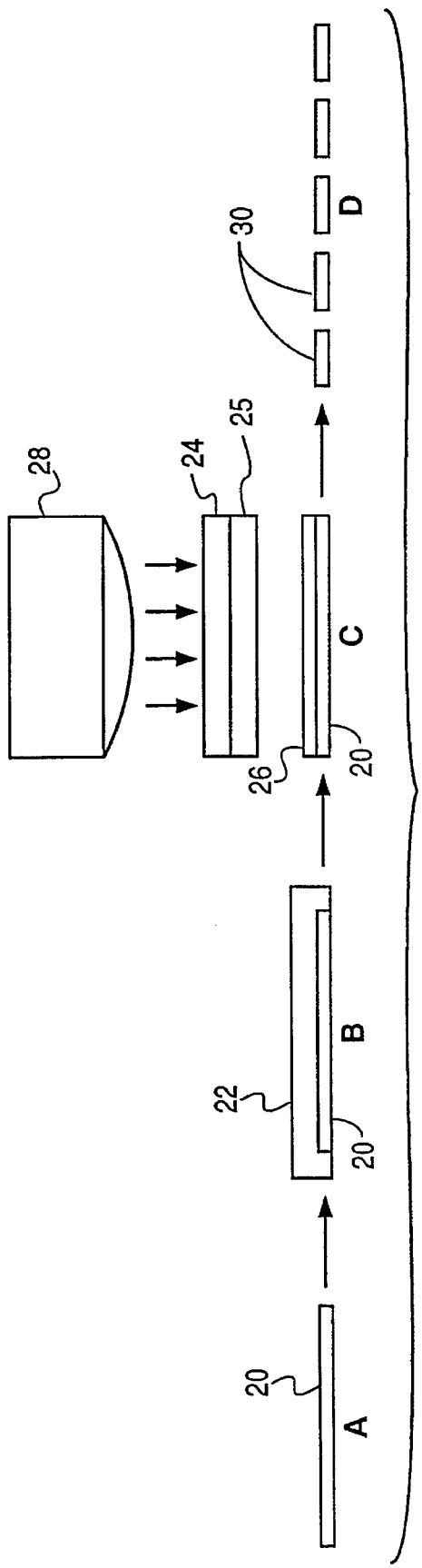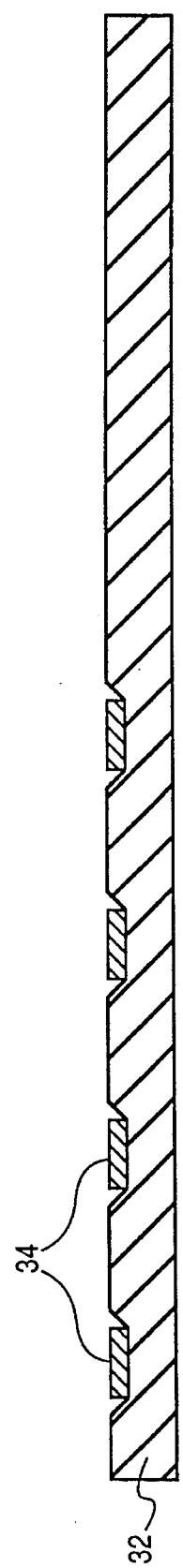

HIGHLY REFLECTIVE BIOGRATINGS

This application is a continuation of application Ser. No. 07/963,249, filed Oct. 19, 1992, now abandoned which was a continuation of Ser. No. 07/525,828, filed May 17, 1990 also now abandoned.

FIELD OF THE INVENTION

This invention relates to improved biogratings for use in a reflective diffraction immunoassay and their method of manufacture. In particular, this invention relates to multilayer biogratings having high reflectivity and high protein binding capacity.

1. Background of the Invention

Many solid-phase binding assays involve surface illumination and consequent light emissions from molecules attached to the surface or are masked by forward scattering. Generally, these emissions travel in all directions. Either these divergent emissions must be collected with expensive and awkward light collection optics to achieve sensitivity, the inherent inefficiencies and consequent low signal to light level ratios must be accepted, or the signal must be measured against a strong background.

Diffraction gratings cause light to be diffracted into specific angles as contrasted to being scattered in all directions. The original diffraction gratings were prepared by ruling a number of straight, parallel grooves in a surface. Incident light was diffracted by each of the surfaces and was principally directed in directions in which light from each groove interferes constructively with light scattered by the other grooves. This constructive light interference property of a grating allows efficient collection of light. Preformed diffraction gratings of this type have been used in binding assay systems.

Many assay systems have been developed using different physically measurable properties of reagents to provide a measurement of an analyte concentration in a sample. Radioimmunoassay (RIA), immunofluorescence, chemiluminescence, enzyme immunoassays (EIA), free radical immunoassays (FRAT), light scattering nephelometry, transistor bridge probes, indium reflective surfaces, and ultrasonic probes have been applied. These systems use the highly selective reaction between a primary member of a binding pair such as an antibody or antigen and an analyte selectively binding therewith. These techniques require expensive measurement equipment and often involve very complicated test procedures.

2. Description of the Prior Art

Reflective and transmissive biograting immunoassay systems and methods were disclosed in U.S. Pat. No. 4,647,544. One embodiment described in the patent uses a biograting, a substantially flat surface having a coating thereon and having substantially uniform light scattering properties. The coating comprises a diffraction grating pattern of alternating parallel linear zones of an active and deactivated binding reagent. The zones form a diffraction grating when the active binding reagent binds with its opposite member of the binding pair. In the absence of such binding, no significant light diffraction occurs, that is, light energy detected at the diffraction angles is at a minimum value, approaching zero. When the binding occurs, the accumulation of bound material in the patterns of a diffraction grating creates a light disturbing grating, and light detected at the light diffraction angles increases to a larger value which correlates to the presence and quantity of the binding partner (analyte) in the sample. The flat surfaces upon which the biograting is formed in the patent include glass, plastic, plastic coating on a solid surface, gel or other suitable inert material onto which specific antibody molecules can be attached.

U.S. Pat. No. 4,876,208 describes transmissive and reflective diffraction binding assays and biograting systems of the type described in U.S. Pat. No. 4,647,544. The biograting supports disclosed in this patent include a smooth upper surface of any material to which a primary hybridizing reagent can be adhered by physical or chemical bonding and which will not interfere with the reactions which are used to determine the presence and extent of the hybridizing reaction. Organic and inorganic polymers, both natural and synthetic, are described. Examples of polymers listed include polyethylene, polypropylene, polybutylene, poly(4-methylbutylene), butyl rubber, silastic polymers, polyesters, polyamides, cellulose and cellulose derivatives (such as cellulose acetate, nitrocellulose and the like), acrylates, methacrylates, vinyl polymers (such as polyvinyl acetate, polyvinyl chloride, polyvinylidene chloride, polyvinyl fluoride, and the like), polystyrene and styrene graft copolymers, rayon, nylon, polyvinylbutyrate, polyformaldehyde, etc. Other materials which are listed are silicon wafers, glasses, insoluble protein coatings on a smooth insoluble surface, metals, metalloids, metal oxides, magnetic materials, materials used in semiconductor devices, cermets and the like. The supports disclosed as preferred include polished single crystalline silicon, aluminum, epitaxial silicon coatings, silicon nitride coatings, silicon dioxide coatings, and polysilicon coatings.

SUMMARY OF THE INVENTION

This invention is directed to improved reflective diffraction biogratings suitable for use in the apparatus and methods of U.S. Pat. Nos. 4,647,544 and 4,876,208, the entire contents of which are hereby incorporated by reference. These biogratings have a higher reflectivity, a high binding capacity and optical flatness.

In summary, the biograting consists of an optically Flat layer of silicon dioxide having a first and second surface, alternating zones of active and inactive binding reagent on the first surface, and a reflective metal layer having a thickness of at least about 1000 Å. The reflective a layer can be supported on an optically flat surface of a wafer, and the reflective metal can be aluminum, gold, silver, chromium, platinum, titanium or nickel coating on a polished wafer. Preferably, the silicon dioxide layer is formed by sputtering a thin layer of silicon dioxide or by coating an alkali metal silicate solution on the surface of the reflective metal. The sputtering can be carried out using conventional sputtering devices and processes, and the thickness of the silicon dioxide can be controlled by varying the discharge time. The alkali metal silicate solution optimally contains from 1 to 20 wt. % and preferably from to 10 wt. % silicon dioxide; from 0.5 to 15 wt. % and preferably from 5 to 10 wt. % of an aminoalkyltrialkoxysilane; and from 1 to 20 and preferably from 5 to 10 mg/ml of a water-soluble polysaccharide. The method for making the biograting comprises uniformly adhering a binding reagent to one surface of an optically flat layer of silicon dioxide, the reflective metal layer being on the second surface; and selectively deactivating zones of the binding reagent to form a diffraction grating pattern of alternating zones of active and deactivated binding reagent by exposing the surface to a deactivating amount of UV light through a transparent mask having a diffraction grating pattern of opaque zones thereon.

An alternative reflective biograting embodiment for a diffraction bioassay device of this invention comprises alternating zones of active and inactive binding reagent on a silicon surface layer of a reflective support. The reflective support comprising one or more reflective layer units, each reflective layer unit comprising an optically flat layer of silicon, and preferably polysilicon, on a layer of silicon dioxide. Each layer of silicon has a thickness within the range of from 150 to 750 Å, from 850 to 1300 Å, or from 1700 to 2150 Å, and preferably within the range of from 200 to 600 Å. Each layer of silicon dioxide has a thickness within the range of from 800 to 1200 Å. The reflective support is supported on the substantially flat surface of an insoluble support.

BRIEF DESCRIPTION OF THE DRAWINGS

FIG. 2 is a schematic representation of the process for manufacturing an insoluble support with the diffraction grating design of FIG. 1.

FIG. 3 is a cross-sectional view of a dipstick having mounted thereon, a plurality of insoluble supports with diffraction grating designs of binding reagents on the surfaces thereof.

DETAILED DESCRIPTION OF THE INVENTION

Figure 1:
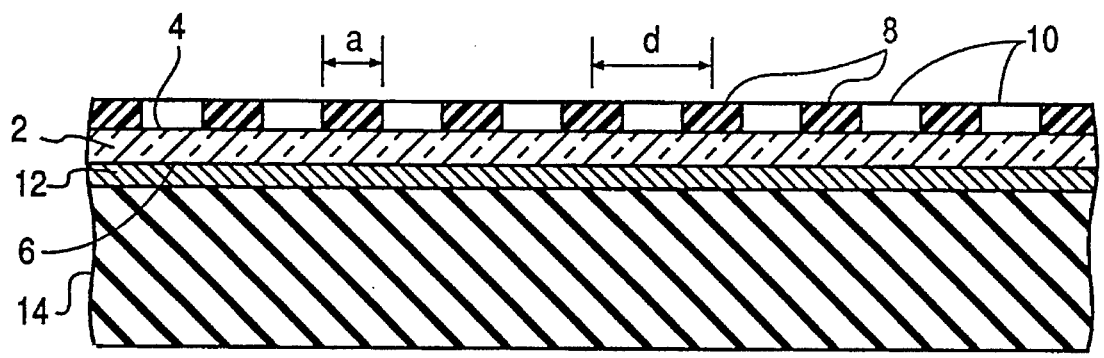
FIG. 1 is a fragmentary, magnified cross-sectional view of one embodiment of this invention.

In an effort to increase the sensitivity of diffraction immunoassay systems using reflective biogratings, a wide variety of surfaces were investigated. The optimum reflective biograting combines high protein binding capacity, optical flatness, and a high reflectivity. Examples of typical normal incidence reflectivities of biogratings found were bare silicon (23%), silicon oxide on silicon (12%), silicon nitride on silicon (1%), glass microscope slide (4%), and polystyrene (7%). With the improved biogratings of this invention, reflectivities greater than 60 percent have been obtained, substantially increasing the sensitivity of the bioassays developed using the improved biograting. The term "biograting", as used herein, is defined to be a substantially flat surface having a coating thereon and having substantially uniform light scattering properties. The coating comprises a diffraction grating pattern of alternating and preferably parallel linear zones of an active and deactivated binding reagent. The zones form a diffraction grating when the active binding reagent binds with its opposite member of the binding pair. In the absence of such binding, no significant light diffraction occurs, that is, light energy detected at the diffraction angles is at a minimum value, approaching zero. When the binding occurs, the accumulation of bound material in the patterns of a diffraction grating creates a light disturbing grating, and light detected at the light diffraction angles increases to a large value which correlates to the presence and quantity of the binding partner (analyte) in the sample.

The term "binding reagent" is used herein to designate one member of any binding pair of compounds or materials which selectively bind to form a conjugate. The members of the binding pair are generically denoted by the terms "ligand" and "antiligand" either one of which can be a binding reagent. The binding reagent can be a member of the well-known antibody-antigen or antibody-hapten pairs wherein the antibody binds selectively with the respective antigen or hapten, or combinations where the antibody is replaced with an Fab, Fab', F(ab')$_2$ fragment or hybrid antibody. The binding reagent can also be a member of other types of binding pairs such as biotin-avidin; lectin-sugar; IgG antibody Fc portion with protein A or protein G; enzyme-enzyme substrate; DNA or RNA binding with DNA, DNA fragments or other nucleotide sequences; enzyme-enzyme inhibitor; protein-protein receptor; chelating agent-ligand; and the like. Also included are specific binding pairs wherein a mercapto group binds specifically with a dithio or disulfide group (—S—SH or —S—S—) or with a N-substituted-2,4-diketo-3-pyrroline group, and other molecules with functional groups that will bind each other specifically. In general, the binding reagent is selected to bind specifically or selectively with the analyte, the material for which a sample is assayed. A non-light disturbing layer or coating of binding reagent is applied to an insoluble surface and is transformed into a diffraction grating design of non-light disturbing material for use in the method of this invention.

The term "binding assay", is used herein to designate an assay using any binding reaction between a binding reagent and the other member of the binding pair which is selectively bindable therewith.

The term "light disturbing", as used herein, is defined to include all ways in which light is affected including light absorbing, reflecting, scattering, refracting and phase changing.

The term "diffraction grating", as used herein, is defined to include gratings which are formed in one or more immunological steps. For the method of this invention, the diffraction grating is formed directly by the conjugation of the non-light disturbing binding reagent on the insoluble surface with a light disturbing analyte. Types of gratings include reflection amplitude gratings, transmission amplitude gratings, reflection phase gratings, and transmission phase gratings. In reflection amplitude gratings, light is reflected from the grating, and the amplitude of the reflected light is modulated by the spatially variable reflection of the grating. In the reflection phase grating, the light is reflected from the grating, and the phase of the reflected light is modulated by the spatially variable refractive index of the grating. In the method of this invention, the diffraction grating may function as one or more of these types of gratings concurrently, and all of these grating types are included within the diffraction gratings made in the method of this invention.

The term "optically flat", as used herein, is defined to be a surface with a maximum height variation of less than 600 Å over a surface area of 4 mm$^2$.

The term "wafer", as used herein, is defined to be a optically flat plate of insoluble solid.

The term "alkyl", as used herein includes saturated and unsaturated, straight, branch-chained and cyclic hydrocarbon groups. The term "lower alkyl" is defined to include alkyl groups having from 1 to 6 carbon atoms.

FIG. 1 is a fragmentary, magnified cross-sectional view of one embodiment of this invention. It consists essentially of an optically flat layer of a transparent material 2 having a first surface 4 and a second surface 6. It has alternating zones of active binding reagent 8 and inactive binding reagent 10 on the first surface, and a reflective metal layer 12 having a thickness of at least about 1000 Å on the second surface 6. The active binding agent zones 8 have a width, a, and a distance between centers of the binding reagent or "period", d.

The reflective metal layer 12 can be any reflective metal which has the stability required for the processing steps and an inherent reflectivity (for polished or optically flat surfaces) of at least 40%. Examples of suitable reflective metals include aluminum, gold, silver, chromium, titanium, nickel and platinum.

The transparent layer or coating 2 can be any transparent material which can bind protein and can be applied as a coating. It can be an organic material such as an organic polymer such as nitrocellulose. It can also be an inorganic material such as a silicon dioxide. The invention is hereinafter described with the use of silicon dioxide for purposes of clarity of description and not by way of limitation. Any transparent material satisfying the above requirements can be used and are considered to be within the scope of this invention.

The silicon dioxide layer can be any optically flat plate of transparent glass containing silicon dioxide, preferably treated with a suitable silane to increase its protein binding capacity. If the silicon dioxide is a self-supporting layer such as a microscope slide or coverslip, for example, the reflective metal can be applied to the surface opposite to the side carrying the biograting in a mirroring, vapor deposition, sputtering or other metallization process.

The combination yielding the highest optical flatness and reflectivity comprises a silicon dioxide coating formed on a reflective metal coated, optically flat wafer 14 of silicon or silicon dioxide. The wafer is the supporting layer and should have the physical and chemical stability to undergo the metallization process without significant change. A convenient source of wafers are polished plates of semiconductor materials such as silicon wafers typically used in semiconductor manufacture. These are readily available in a polished, optically flat form and have the thermal and chemical stability for metallization by vapor deposition or metal sputtering, both conventional and well known processes commonly used in semiconductor manufacture. However, polished glass would be equally suitable as a substrate since no radiation penetrates the metal layer.

The optimum reflective metal coating process depends upon the particular metal used. Aluminum, gold and silver coatings can be directly applied to one surface of the support wafer in a sputtering process carried out in an inert atmosphere, usually in a partial vacuum. The coating thickness is controlled to be sufficient to reflect all incident light, that is, at least about 1000 Å. Suitable processes for depositing the metal coatings, for example sputtering and vapor deposition, are described in VLSI TECHNOLOGY, Edited by S. M. Sze, New York: McGraw-Hill (1983).

The silicon dioxide coating is then applied to the reflective metal surface by a process which yields a product having a high reflectivity and an optically flat surface. The silicon dioxide coating can be applied by sputtering, as described in VLSI TECHNOLOGY (supra, p 358). Alternatively, the silicon dioxide coating can be applied by spin coating the reflective surface with an alkali metal silicate solution. Spin coating is a conventional process, well known to a person skilled in the coating art. The thickness of the coating is determined by the viscosity of the alkali metal silicate solution, spinning speed, temperature and evaporation rate. In general, the surface is spun around an axis perpendicular to the surface, and the solution is applied either before or during the spinning. If the coating is applied to a conventional circular wafer disk having a diameter of 4 inches, the spinning speed should be from 1500 to 8000 rpm and preferably is from 2500 to 4000 rpm.

The alkali metal silicate solution can be made of any alkali metal (sodium, potassium, lithium, etc) and is preferably a conventional sodium silicate (water glass) solution containing from 1 to 20 wt. % and preferably from 5 to 10 wt. % alkali metal silicate.

Protein binding capacity of the silicon dioxide product is increased if the surface is treated with a protein binding reagent such as an aminosilane. If the silicon dioxide coating is formed from an alkali metal silicate solution, the protein binding reagent can be incorporated directly in the coating solution. Suitable aminosilanes include aminoalkylsilanes having the formula:

wherein, $R_1$ is hydrogen, an aminoalkyl group having from 1 to 18 carbons, or an aminoalkylamino group having from 1 to 18 carbons; and $R_2$, and $R_3$ are each, individually, a lower alkyl or alkoxy group.

Examples of suitable aminoalkylsilanes include aminopropyltriethoxysilane, aminopropyltrimethoxysilane, aminobutyltriethoxysilane, N-(2-aminoethyl-3-aminopropyl)triethoxysilane, ω-aminoundecyltrimethoxysilane, and aminopropylmethyldiethoxysilane, for example. A preferred aminoalkyltrialkoxysilane is N-(2-aminoethyl-3-aminopropyl)triethoxysilane. The alkali metal silicate solution can contain from 0.5 to 15 wt. % and preferably from 5 to 10 wt. % of the aminoalkylsilane.

The binding capacity is further increased if the alkali metal silicate solution also includes from 1 to 20 mg/ml and preferably from 5 to 10 mg/ml of a water soluble hydroxylated polymers, preferably polysaccharides. Suitable polysaccharides include water-soluble gums, hydrolyzed starches, cellulose derivatives, and other conventional water-soluble hydroxylated polymers. A particularly suitable polysaccharide are the dextrans having a molecular weight of from 5000 to 500,000 and preferably from 10,000 to 75,000.

The silicon dioxide coating thickness is determined by the sputtering time in the sputter coating process or by the speed of rotation in the spin coating process. The thickness of the silicon dioxide coating can be from 100 Å to 3000 Å and is preferably from 250 Å to 1000 Å.

If the silicon dioxide coating is applied as an alkali silicate solution, for thin coatings, the coated support is cured by heating in an oven at a temperature of from 90° to 200° C. and preferably from 120° to 150° C. for a time sufficient to cure the coating. The heating time will depend upon the thickness of the coating and the concentration of the coating solution. A heating time of from 0.5 to 16 hours is sufficient. A heating time of from 1 to 3 hours is preferred.

The method for making the biograting comprises a first step of uniformly adhering a binding reagent to the silicon dioxide surface. This followed by a step of selectively deactivating zones of the binding reagent to form a diffraction grating pattern of alternating zones of active and deactivated binding reagent by exposing the surface to a deactivating amount of UV light through a transparent mask having a diffraction grating pattern of opaque zones thereon.

The binding reagent applied to the silicon dioxide surface of an insoluble support is selected to bind with the analyte to be determined in the assay. It can be any member of the binding pairs described above. It can be an antibody; antibody fragment selected from the group consisting of Fab, Fab', or F(ab')$_2$ fragments; hybrid antibody; antigen; hapten; protein A; protein G; lectin; biotin; avidin; chelating agent; enzyme; enzyme inhibitor; protein receptor; nucleotide hybridizing agent; or a bacteria, virus, Mycoplasmatales, spore, parasite, yeast, or fragment thereof; or combinations thereof.

FIG. 2 is a schematic representation of the process for manufacturing an insoluble support with the diffraction grating design of FIG. 1. One member of the binding pair can be applied to the silicon dioxide surface 20 (Step A) by covalent bonding or adsorption in solution 22 in Step B. For covalent bonding, the surface, after being coated with an aminosilane, can be reacted with the protein.

One procedure for conjugating aminosilane groups with proteins can be achieved with 1-ethyl-3-(3-dimethylaminopropyl)-carbodiimide (EDCI). This is a water-soluble carbodiimide which is used for coupling antibodies or proteins with haptens or solid phases through functional groups such as carboxy and/or amino groups. EDCI reactions can be carried out as follows: To a solution of antigen or antibody in 0.01M phosphate buffered saline, pH 6.0 at 4° C., is added an excess amount (normally 100 times the stoichiometric amount) of EDCI. The insoluble support having amino groups thereon, is added to the solution. After addition, the mixture is stirred at refrigerated temperatures for 16–24 hours to complete the reaction.

If the protein to be coupled to the support is an antibody, the conjugation is preferably carried out with a soluble periodate such as an alkali metal periodate. To a solution of antibody in 0.2M acetate buffer, pH 5, is added a solution of the periodate (11.2 mg of periodate per 1 mg of antibody). The mixture is stirred at 4–8° C. for 1 to 1.5 hours. It is then dialyzed against 0.1M carbonate buffer, pH 8.9, and the resulting solution is incubated with the insoluble support in a refrigerator overnight.

The antibodies can also be coupled to the insoluble surface through a thioether linkage. In this procedure, the aminopropyltriethoxysilane activated surface is allowed to react with an excess amount of iodoacetic anhydride or bromoacetic anhydride in anhydrous dimethylformamide at room temperature overnight while protecting the reactants from light. The activated surface is then washed thoroughly with deionized water and kept protected from light exposure until it is reacted with the antibody. Before being reacted with the iodoacetyl or bromoacetyl activated surface, the antibody is treated with 2-aminoethanethiol at 37° C. for 2 hours in a degassed 0.1M phosphate buffer solution, pH 6.0. After the reaction with 2-aminoethanethiol, the solution is chromatographically purified with a Sephadex column (Pharmacia) to remove the excess amount of 2-aminoethanethiol. The antibody reaction product has mercapto groups. It can be coupled to the solid surface by reacting the solution with the iodoacetyl or bromoacetyl activated surfaces at refrigerated temperatures overnight.

Non-covalent bonding can be achieved by immersing the surface in an aqueous buffer solution. The buffered binding reagent solution is placed in a container containing the silicon dioxide surface and incubated at room temperature until adsorption occurs, for example for from 0.5 to 18 hours and preferable from 1 to 3 hours, at temperatures of from 4° to 40° C. and preferable from 20° to 26° C. The surface is then rinsed with a buffered saline solution and dried.

The concentration of binding reagent in the buffer solution is selected to provide the desired reagent density on the silicon dioxide surface. The binding reagent solution can contain from 0.02 to 100 micrograms/ml of the binding reagent and preferably contains from 10 to 50 micrograms/ml of the binding reagent in a buffered solution having a pH of from 6.0 to 9.5 and preferably from 7.0 to 8.5. The surface with the coating 26 thereon is then rinsed and dried.

A suitable rinse solution is an aqueous phosphate buffer solution such as is described in U.S. Pat. No. 4,528,267 having a phosphate molarity of from 0.0001 to 0.05, a pH of from 6 to 8 and containing from 0.001 to 0.1 weight percent non-ionic surfactant and from 0.0001 to 0.5 weight percent of an animal serum albumin. Suitable non-ionic surfactants include polyoxyethylene ethers (BRIJ) such as lauryl, cetyl, oleyl, stearyl, and tridecyl polyoxyethylene ethers; polyoxyethylenesorbitans (TWEEN) such as polyoxyethylenesorbitan monolaurate, monopalmitate, monostearate, monooleate and trioleates; and other polyoxyethylene ethers (TRITON), for example. Preferred non-ionic surfactant are the polyoxyethylenesorbitans such as polyoxyethylenesorbitan monolaurate (TWEEN 20).

A mask is prepared by photographic methods conventional in semiconductor manufacturing. For example, a mask having a plurality of diffraction gratings having the desired line density and line widths can be prepared on a quartz glass or other UV-transparent plate through a photoresist process similar to photography. The dark zones, preferably linear zones or lines, of the mask correspond to active binding reagent areas desired on the ultimate surface.

In Step C, the mask 24 is mounted in a suitable support 25 of a UV light focusing apparatus such as a Karl Suss Model 40 Mask Aligner (Karl Suss, Waterbury Center, Vt. 05677). The mask 24 is placed over the silicon dioxide surface 20 having a coating 26 of binding reagent, and the surface is exposed to ultraviolet radiation from UV radiation source 28 until the binding capability of the portions of the binding reagent exposed to the radiation is substantially reduced or preferably eliminated. To manufacture a precision grating design, the radiation should form a sharp image on the coated surface. Penumbrae should be minimized. Preferably, the ultraviolet light passing through the mask is focused to a sharp image on the surface coating using conventional projection alignment techniques without contact with the coated surface.

The ultraviolet radiation exposure required to deactivate coating exposed thereto depends upon the binding reagent. For antibody binding reagents, exposure times of from 30 sec to 30 min and preferably from 1 to 5 min is sufficient with a ultraviolet radiation having a wavelength such as 254 nm and a power of from 8 to 14 milliwatts per cm$^2$. Some adjustment in time of exposure and/or power may be necessary to deactivate the binding sites of other binding reagents.

To alter the epitopes of antigenic binding reagents such as human IgG, exposure times of from 5 to 30 min and preferably from 5 to 10 min are sufficient with a ultraviolet radiation having a wavelength of 254 nm and a power of from 8 to 14 milliwatts per cm$^2$. Some adjustment in time of exposure and/or power may be necessary to alter or destroy the antigenic sites of other binding reagents.

This treatment reduces or eliminates the binding properties of the binding reagent in zones 10, leaving active binding reagent in a diffraction grating design as the zones 8 (FIG. 1).

In Step D, the coated substrate containing areas having binding protein in a diffraction grating design is cut into smaller area chips 30, each chip having a size sufficient to perform a binding assay. These chips are then mounted on a suitable diagnostic support such as the dipstick shown in FIG. 3.

FIG. 3 is a cross-sectional view of a dipstick having mounted thereon, a plurality of insoluble supports with non-light disturbing diffraction grating designs of binding reagents on the surfaces thereof. The dipstick body 32 has a plurality of insoluble support surfaces 34 having a diffraction grating design of binding reagent coated thereon such the biogratings shown in FIG. 1 made by the process shown in FIG. 2. The materials from which the dipstick 32 are made are preferably non-binding to minimize non-specific binding during the binding assay procedure. Suitable dipstick surface materials include polyolefins such as polyethylene and polypropylene, hydrophilic polysilicon and polysiloxane polymers, and the like. Also suitable are polymers which have been treated to render the surfaces non-binding to proteinaceous materials. The silanes can be applied to the silicon dioxide surface in a vapor phase, for example.

The support for the diffraction grating supports can be any articles upon which the diffraction grating support surface can be mounted. The description of dipsticks are provided by way of example, and not as a limitation. Other articles such as microwells, plates, cavities and the like can be used. For many applications, dipsticks are a preferred embodiment.

Figure 4:
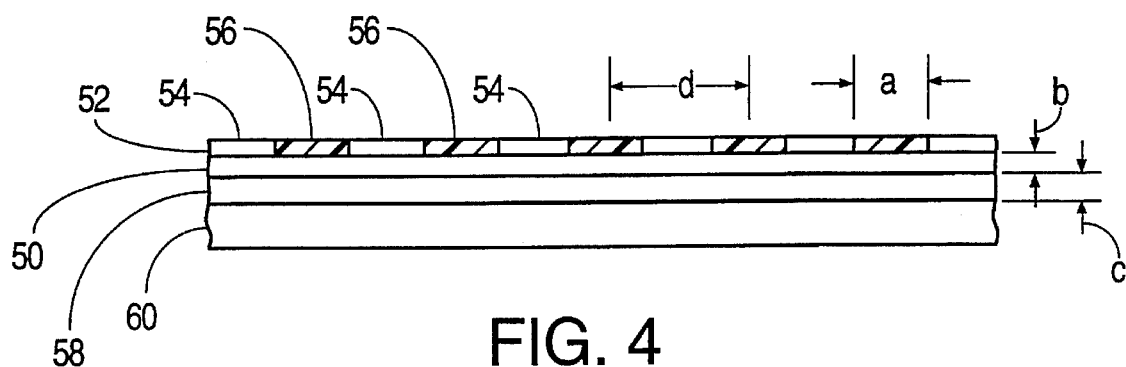
FIG. 4 is a fragmentary, magnified cross-sectional view of an alternate embodiment of this invention, with a single silicon-silicon dioxide reflective layer unit supporting a biograting.

FIG. 4 is a fragmentary, magnified cross-sectional view of the alternate embodiment, using a reflective support comprising a single reflective layer unit. An optically flat surface 50 of silicon and preferably polysilicon supports the binding reagent layer 52. As described above with respect to the embodiment of FIG. 1, the binding layer provides a diffraction grating design or pattern of active binding reagent. The diffraction grating design comprises a plurality of zones of non-light disturbing active binding reagent 54 separated by zones of non-light disturbing deactivated binding reagent 56, for example, binding reagent which has been deactivated by exposure to ultraviolet radiation, other deactivating radiation, or other deactivation energy. The binding reagent is a member of a binding pair as described above.

As with the embodiment of FIG. 1, the active binding reagent zones have a width, a, and a distance between centers of the binding reagent or "period", d.

The silicon layer 50 has a thickness, b. It is supported by and is preferably a coating on an optically flat surface of a silicon dioxide 58, having a thickness, c. The combination of the silicon layer 50 and silicon dioxide layer 58 constituting a single "reflective layer unit". The reflective layer is supported by an optically flat surface of an insoluble support such as a wafer and is preferably a series of coatings on the insoluble support. The wafer is the supporting layer and should have the physical and chemical stability to undergo the coating process without significant change. A convenient source of wafers are polished plates of semiconductor materials such as silicon wafers typically used in semiconductor manufacture. These are readily available in a polished, optically flat form and have the thermal and chemical stability for coating by conventional chemical vapor deposition.

Figure 5:
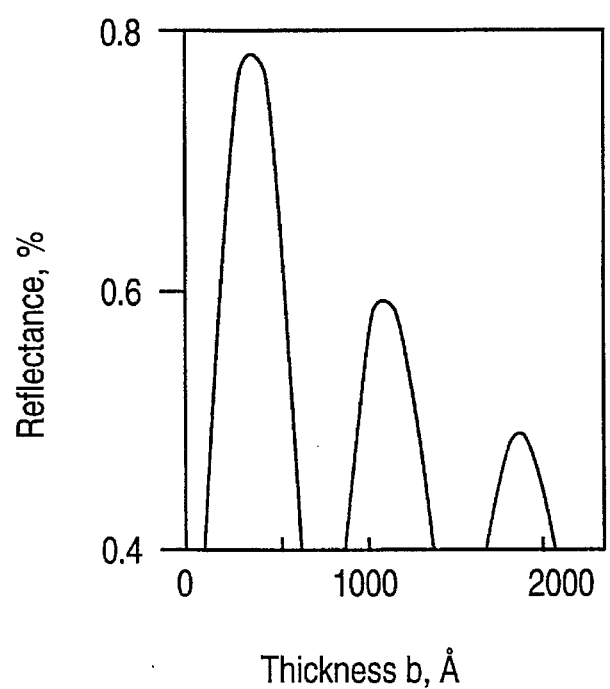
FIG. 5 is a graph showing the relationship between the thickness of the silicon layer of the single reflective layer unit embodiment of this invention and the percent reflectivity.

As shown in FIG. 5, the thickness, b, of the silicon layer, 50, is critical for obtaining high reflectivity. The reflective layer provides a reflectivity of 40 percent and higher if the silicon layer has a thickness within the range of from about 150 to 750 Å, from about 850 to 1300 Å, or from about 1700 to 2150 Å. The reflective layer provides a reflectivity of 60 percent and higher if the silicon layer has a thickness within the range of from about 200 to 600 Å. A reflectivity of almost 80 percent is provided if the silicon layer has a thickness of about 250 to about 400 Å.

To provide optimum reflectivity, the silicon dioxide layer 58 should have a thickness, c, which is within the range of from 800 to 1200 Å and is preferably within the range of from 950 to 1050 Å.

The biograting embodiment shown in FIG. 4 is formed by applying the desired thickness of silicon dioxide 58 to the optically flat surface of the wafer 60, preferably by a conventional chemical vapor deposition process. A layer of silicon such as polysilicon having the desired thickness is then deposited on the silicon dioxide surface, preferably by a conventional vapor deposition process. Suitable procedures applying coatings of epitaxial silicon, polysilicon, and silicon dioxide by vapor deposition are described by VLSI TECHNOLOGY (supra) and P. V. Zant, MICROCHIP FABRICATION: A PRACTICAL GUIDE TO SEMICONDUCTOR PROCESSING. San Jose: Semiconductor Services (1984). The entire contents of these books and the publications cited therein are hereby incorporated by reference.

The biograting coating and UV exposure to form the diffraction grating pattern are applied as described above with respect to the embodiment of FIG. 2.

Figure 6:
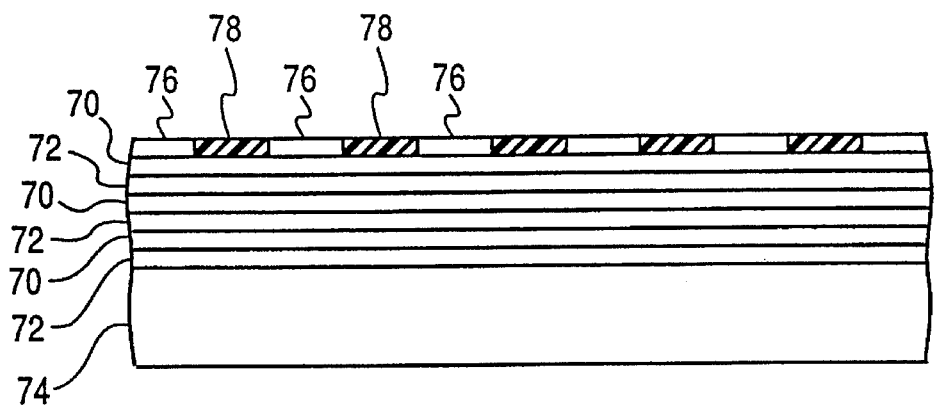
FIG. 6 is a fragmentary, magnified cross-sectional view of an alternate embodiment of this invention, with a plurality of reflective layer units.

FIG. 6 is a fragmentary, magnified cross-sectional view of an alternate embodiment of this invention, with a plurality of reflective layer units. Each reflective layer unit comprises a layer of silicon 70 and a layer of silicon dioxide 72 having the critical thicknesses described above with respect to the embodiment of FIG. 4. The bottom reflective layer unit is supported on the optically flat surface of a wafer 74. Each successive reflective layer unit provides an incremental increase to the reflectivity. Although no theoretical limit to the number of reflective layer units exists, the amount of the reflectivity increase provided with each additional unit is incrementally smaller, and no significant advantage is obtained with more than five reflective layer units. Most of the practical increases in reflectivity are obtained with three reflective layer units, the configuration shown in FIG. 6.

As described above with respect to the embodiment of FIG. 1, the binding layer provides a diffraction grating design or pattern of active binding reagent. The diffraction grating design comprises a plurality of zones of non-light disturbing active binding reagent 76 separated by zones of non-light disturbing deactivated binding reagent 78, for example, binding reagent which has been deactivated by exposure to ultraviolet radiation, other deactivating radiation, or other deactivation energy. The binding reagent is a member of a binding pair as described above.

This invention is further illustrated by the following specific but non-limiting examples. Examples which have been reduced to practice are stated in the past tense, and examples which are constructively reduced to practice herein are presented in the present tense. Temperatures are given in degrees Centigrade and weight as weight percents unless otherwise specified.

EXAMPLE 1

Aluminum Coated Silicon Surface

Bare silicon wafers are placed in a high frequency magnetron sputtering chamber, the chamber evacuated to $5 \times 10^{-6}$ torr, argon gas is introduced, and the plasma glow discharge is initiated to deposit aluminum on the silicon wafer surface using the procedures of VLSI TECHNOLOGY (supra) and MICROCHIP FABRICATION: A PRACTICAL GUIDE TO SEMICONDUCTOR PROCESSING, (supra). After 35 minutes, the plasma is terminated, the chamber vented, and the aluminum coated wafer removed.

EXAMPLE 2

Silicon Dioxide Coated Al/Si Support

The product of Example 1 is placed in a high frequency magnetron sputtering chamber, the chamber evacuated to $5\times10^{-6}$ torr, and plasma gas is introduced. A plasma glow is initiated to clean the aluminum surface. Then a silicon dioxide target is introduced or exposed, and after the desired silicon dioxide coating is formed on the aluminum surface, about 30 minutes, the plasma is terminated, the vessel vented, and the silicon dioxide coated aluminum-on-silicon wafers are removed.

EXAMPLE 3

APTS coated $SiO_2$/Al/Si Support

Aminopropyltriethoxysilane (APTS) is coated onto a silicon dioxide/aluminum/silicon wafer by vapor deposition. The wafer is placed in a vacuum oven, the oven heated to 170° C., and the chamber evacuated to about 0.1 torr. The aminopropyltriethoxysilane is introduced into the oven, allowed to vaporize, and the coating process is continued for 4 hr. The oven is evacuated to remove remaining aminopropyltriethoxysilane vapor, and the wafer is retained in the oven for 8 hr to complete the coating reaction. The oven is then vented, and the APTS coated $SiO_2$/Al/Si wafer is removed.

EXAMPLE 4

Sodium Silicate Coating on Al/Si Support

A 3.1 molar sodium silicate solution (VMR Scientific Catalog No. Ala. 68330) was diluted 1:4 with deionized water, and pipetted onto an aluminum coated silicon wafer. The wafer was spun with a Model 6000 spin coater (Integrated Technologies, Inc. Asushnet, Mass. 02743) at 3000 rpm for one min. The silicate coated wafer was then cured in an oven at 135° C. for 2 hr and allowed to cool to room temperature.

EXAMPLE 5

APTS/SILICATE Coating on Al/Si Support

A mixture of 3.1 molar sodium silicate solution, aminopropyltriethoxysilane, and deionized water (1:0.5:3.5 v/v/v) was prepared. The solution was pipetted onto an aluminum coated silicon wafer. The wafer was spun with a Model 6000 spin coater (Integrated Technologies, Inc. Asushnet, Mass. 02743) at 3000 rpm for one min. The silicate coated wafer was then cured in an oven at 135° C. for 2 hr and allowed to cool to room temperature.

EXAMPLE 6

APTS-DEXTRAN-SILICATE Coating on Al/Si Support

To each ml of a mixture of 3.1 molar sodium silicate solution, aminopropyltriethoxysilane, and deionized water (1:0.5:3.5 v/v/v) was added 5 mg of dextran (50,000 daltons). The mixture was pipetted onto a aluminum coated silicon wafer. The wafer was spun with a Model 6000 spin coater (Integrated Technologies, Inc. Asushnet, Mass. 02743) at 3000 rpm for one min. The silicate coated wafer was then cured in an oven at 135° C. for 2 hr and allowed to cool to room temperature.

EXAMPLE 7

Reflectivities of Coated Al/Si Supports

The reflectivities of the silicon surfaces prepared in Examples 1–6 were determined. The silicon surfaces were illuminated with a Model 1107P Helium-Neon Laser (Uniphase, Sunnyvale, Calif. 94086) at an incident angle of 75°. The reflected light intensity was measured with a Model 61 Optometer (United Detector Technology, Hawthorne, Calif.). A reflectivity of 80% or higher was found on all surfaces.

| Surface Coating | Reflectivity |
| --- | --- |
| Silicon Dioxide | 0.92 |
| APTS/Silicon Dioxide | 0.84 |
| Silicate | 0.85 |
| APTS/Silicate | 0.80 |
| APTS/Silicate/Dextran | 0.80 |

EXAMPLE 8

Monoclonal Anti-β-hCG (Fab) Coating

A silicon dioxide/aluminum/silicon wafer, coated by vapor deposition with APTS, was incubated with a solution of monoclonal anti-β-hCG (Fab) in 0.01M phosphate buffer, pH 7.4 (100 µg/ml) at 4°–8° C. for 4 hr. The surface was briefly washed with 0.05M Tris buffer, pH 8.5, containing 2.5% sucrose. It was then incubated with 0.05M Tris buffer, pH 8.5, containing 2.5% sucrose and 0.5 wt. % human serum albumin (HSA) at 4°–8° C. for 30 min. The residual liquid was removed by spinning the wafer to yield an anti-β-hCG coated silicon dioxide surface.

EXAMPLE 9

Monoclonal Anti-β-HCG (IgG) Coating Monoclonal anti-β-hCG antibody was diluted in 0.2M of acetate buffer, pH 5.0, to a concentration of 2 mg/ml. The solution was cooled in an ice bath, and a solution of sodium periodate (22.4 mg/ml) in 0.1M acetate buffer was slowly added. The mixture was then stirred at 4°–8° C. for to 1.5 hr and then dialyzed against 2 L of 0.1M carbonate buffer, pH 8.9, at 4°–8° C. for 4–6 hr. The antibody solution obtained was incubated with a silicon dioxide/aluminum coated silicon wafer surface which has been coated with APTS by vapor deposition in a refrigerator overnight. The surface was briefly washed with 0.05M Tris buffer, pH 8.5, containing 2.5% sucrose. It was then incubated with 0.05M Tris buffer, pH 8.5, containing 2.5% sucrose and 0.5 wt. % human serum albumin (HSA) at 4°–8° C. for 30 min. The residual liquid was removed by spinning the wafer to yield an anti-β-hCG coated silicon dioxide surface.

EXAMPLE 10

Biograting Preparation

An anti-β-hCG coated silicon dioxide surface prepared by the procedure of Example 8 was placed under a photomask using a Karl Suss Model 40 Mask Aligner. The photomask has parallel opaque lines having a center-to-center distance, d, of 10 µm. The surface was illuminated with UV light at 254 nm for 6 min. After illumination, the surface was diced into 4×6 mm chips.

EXAMPLE 11

Anti-β-hCG (Fab) Biograting Immunoassay

Figure 7:
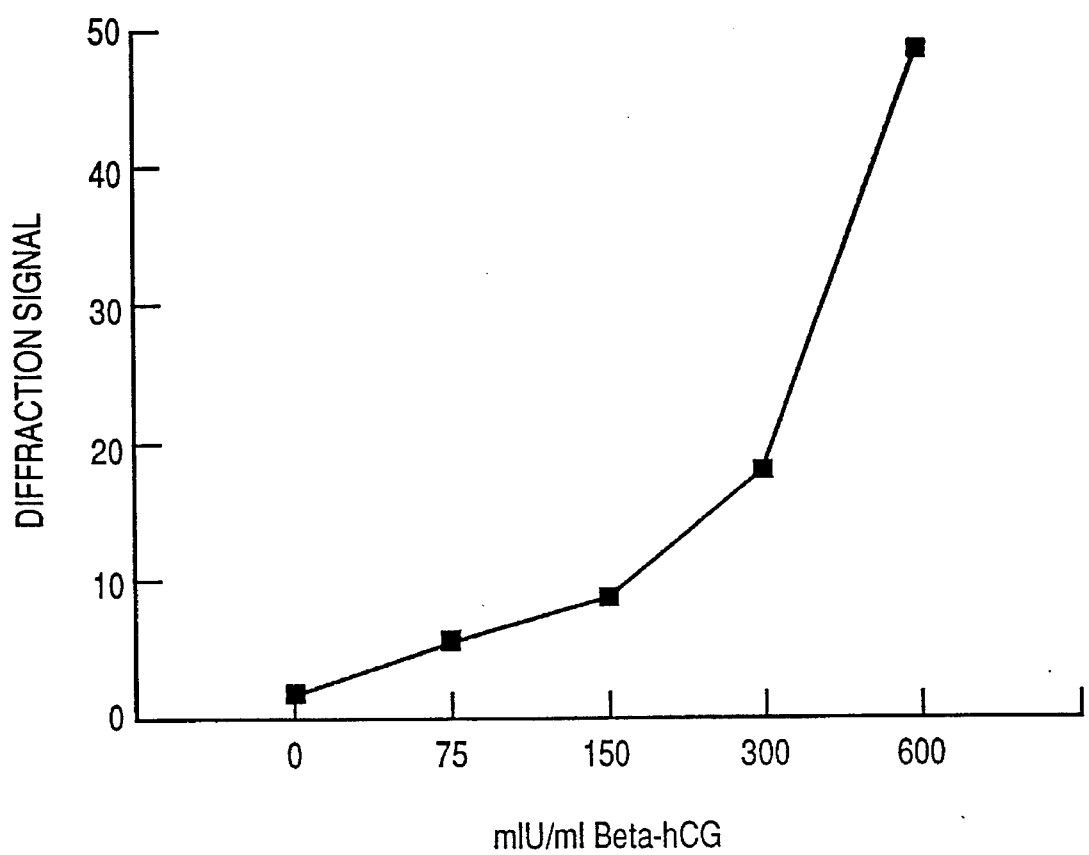
FIG. 7 is a dose response curve showing data obtained in Example 11.

The 4×6 mm chips prepared in Example 10 were mounted on a microscope slide and incubated with 600, 300, 150, 75 and 0 mIU/ml of β-hCG solutions (test samples) at room temperature for 5 min. The surface was washed with deionized water and dried with a stream of air. The diffraction intensities of the surfaces were determined with a Model 61 optometer to give a dose response curve shown in FIG. 7.

We claim:

1. A reflective biograting comprising an optically flat layer of a transparent composition of about 100 to 3000 Å having a first and second surface, alternating zones of active and inactive binding reagent on the first surface, and a reflective metal layer having a thickness of at least about 1000 Å on the second surface, said metal layer having an inherent reflectivity of at least about 40%.

2. The reflective biograting of claim 1 wherein the reflective metal layer is supported on an optically flat surface.

3. The reflective biograting of claim 1 wherein the reflective metal is aluminum, gold, silver, chromium, platinum, nickel or titanium.

4. The reflective biograting of claim 1 wherein the transparent composition layer comprises silicon dioxide.

5. The reflective biograting of claim 1 wherein the transparent composition layer is about 250 to 1000 Å.

6. The reflective biograting of claim 1 wherein the transparent composition layer comprises an alkali metal silicate.

7. The reflective biograting of claim 6 wherein the transparent composition layer is about 1000 Å.

8. The reflective biograting of claim 6 wherein the alkali metal silicate solution contains from 1 to 20 mg/ml of a water-soluble hydroxylated polymer.

9. The reflective biograting of claim 8 wherein the hydroxylated polymer is a dextran having a molecular weight in the range of from 5000 to 500,000.

* * * * *